United States Patent

Brossmer et al.

[11] Patent Number: 5,962,745
[45] Date of Patent: Oct. 5, 1999

[54] PROCESS FOR PREPARING 3-HYDROXYALKANALS

[75] Inventors: Christoph Brossmer, Frankfurt, Germany; Dietrich Arntz, Mobile, Ala.

[73] Assignee: E. I. du Pont de Nemours and Company, Wilmington, Del.

[21] Appl. No.: 09/022,011

[22] Filed: Feb. 11, 1998

Related U.S. Application Data

[60] Provisional application No. 60/054,877, Aug. 6, 1997.

[30] Foreign Application Priority Data

Feb. 14, 1997 [DE] Germany .............................. 197 05 714

[51] Int. Cl.$^6$ ..................................................... C07C 45/61
[52] U.S. Cl. ........................... 568/491; 568/458; 568/485; 568/496; 568/862; 562/11; 562/571; 546/329; 546/335
[58] Field of Search ..................................... 568/491, 496, 568/862, 458, 485; 562/11, 571; 546/329, 335

[56] References Cited

U.S. PATENT DOCUMENTS

| | | | |
|---|---|---|---|
| 2,434,110 | 1/1948 | Hatch et al. .............................. | 260/602 |
| 5,171,898 | 12/1992 | Arntz et al. .............................. | 568/862 |
| 5,284,979 | 2/1994 | Haas et al. ................................ | 568/491 |

FOREIGN PATENT DOCUMENTS 0 544 118   6/1993   Germany .

*Primary Examiner*—Shailendra Kumar
*Assistant Examiner*—Sreeni Padmanashan

[57] ABSTRACT

A process for preparing 3-hydroxyalkanals having 3 to 12 carbon atoms by hydration of 2-alkenals with homogeneous catalysis, by using as catalyst a compound corresponding to the formula

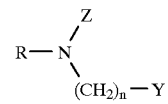

wherein:

z denotes H, $C_1$- to $C_6$-alkyl, —$CH_2$—$CH(CH_3)$ —Y' or —$(CH_2)_o$—Y'

R denotes H, $C_1$- to $C_6$-alkyl, benzyl, phenyl, ω-hydroxy —$C_1$- to $C_6$-alkyl, —$CH_2$—$CH(CH_3)$—Y' or —$(CH_2)_o$—Y'

Y and Y' are identical or different and denote —COOH, —P(O) $(OH)_2$, —OH, pyridyl, or —P(O) $(CH_2OH)$ OH, wherein the acid functional group may be present partly in the form of its alkali metal salt, alkaline-earth salt or ammonium salt n denotes 1, 2, 3, 4, 5 or 6 where Y is —COOH, —P(O) $(OH)_2$, pyridyl or —P(O) $(CH_2OH)$ OH; 2 or 3 where Y is —OH o denotes 1, 2, 3, 4, 5 or 6 where Y' is —COOH, —P(O) $(OH)_2$, pyridyl or —P(O) $(CH_2OH)OH$; 0, 2 or 3 where Y' is —OH.

4 Claims, No Drawings

PROCESS FOR PREPARING 3-HYDROXYALKANALS

This application claims benefit of Provisional application Ser. No. 60/054,877, filed Aug. 6, 1997.

CROSS-REFERENCE TO RELATED APPLICATION

This application claims priority from German Application No. 197 05 714.4 filed on Feb. 14, 1997, the subject matter of which is hereby incorporated herein by reference.

FIELD OF THE INVENTION

This invention relates to a process for preparing 3-hydroxyalkanals having 3 to 12 carbon atoms, by hydration of a 2-alkenal with water in the presence of a catalyst in homogeneous phase.

BACKGROUND OF THE INVENTION

It is known that 2-alkenals corresponding to the general formula $H_2C=CR-CHO$ wherein R is hydrogen or alkyl, such as, for example, acrolein or methacrolein, can be hydrated to the is corresponding 3-hydroxyalkanals in homogeneous phase with water in the presence of acid catalysts (U.S. Pat. No. 2,434,110). 3-Hydroxypropionaldehyde can be prepared from acrolein in this way. 3-Hydroxypropionaldehyde can be further processed by means of hydrogenation to form 1,3-propanediol, which is gaining increasing importance as a monomeric structural unit for polyesters and polyurethanes. The process described in the document U.S. Pat. No. 2,434,110 has the disadvantage that only a low yield and a low selectivity can be achieved.

The use of carbon dioxide as catalyst is known from the document GB-A 1185615. Because of the very long reaction time, however, only very low space-time yields can be achieved.

A process for the hydration of 2-alkenals in a homogeneous medium, in which an acid-base buffer is used as catalyst, is known from the document EP-B 0 544 118. However, the known process has the disadvantage that the space-time yield obtained is not sufficient.

The documents U.S. Pat. No. 3,536,763 and DE-A 3,926,136 disclose processes for the hydration of 2-alkenals wherein heterogeneous catalysts, such as for example ion-exchange resins, are used. But the disadvantage of these processes is that they require a filtration step during the working up of the reaction mixture.

SUMMARY OF THE INVENTION

The object was accordingly to develop a process for preparing 3-hydroxyalkanals by hydration of 2-alkenals by means of a homogeneous catalyst and with a good space-time yield.

This invention provides a process for preparing 3-hydroxyalkanals having 3 to 12, in particular 3 or 4, carbon atoms, by hydration of a 2-alkenal with water in the presence of a catalyst in homogeneous phase at a reaction temperature of from 10° to 100° C., at a pressure of from 1 bar to 20 bar, at an initial concentration of the 2-alkenal in the reaction mixture of from 3 to 30 wt. %, wherein the catalyst used is a compound corresponding to the formula

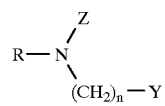

wherein

Z denotes H, $C_1$- to $C_6$-alkyl, $-CH_2-CH(CH_3)-Y'$ or $-(CH_2)_o-Y'$

R denotes H, $C_1$- to $C_6$-alkyl, benzyl, phenyl, ω-hydroxy-$C_1$- to $C_6$-alkyl, $-CH_2-CH(CH_3)-Y'$ or $-(CH_2)_o-Y'$ Y and Y' are identical or different and denote $-COOH$, $-P(O)(OH)_2$, $-OH$, pyridyl, or $-P(O)(CH_2OH)OH$, wherein the acid functional group may be present partly in the form of its alkali metal salt, alkaline-earth salt or ammonium salt n denotes 1, 2, 3, 4, 5 or 6 where Y is $-COOH$, $-P(O)(OH)_2$, pyridyl or $-P(O)(CH_2OH)OH$; 2 or 3 where Y is $-OH$ o denotes 1, 2, 3, 4, 5 or 6 where Y' is $-COOH$, $-P(O)(OH)_2$, pyridyl or $-P(O)(CH_2OH)OH$; 0, 2 or 3 where Y' is $-OH$.

In a preferred embodiment of the invention, a compound from the group a) iminodiacetic acid, iminodipropionic acid and salts thereof, b) iminodimethylphosphonic acid and salts thereof, or c) N-phosphonomethylglycine and salts thereof may be used as catalyst.

The catalysts usable according to the invention are known compounds and are obtainable commercially. Iminoacids are described, for example, in: A. H. Blatt, Org. Synth., 1974, collective vol. 2, 397. Iminodipropionic acid is described in: J. H. Ford, J. Am. Chem. Soc. 67 (1945) 876; iminodimethylphosphonic acid is described in: K. Moedritzer, Synth. Inorg. Met.-Org. Chem. 3 (1973) 75. N-phosphonomethylglycine is the active ingredient of a known herbicide (for example, in EP-A 0162035 B1), which is marketed in the form of its ammonium salt under the names ROUND.UP® and GLYPHOSATE®.

The 2-alkenals are preferably acrolein and methacrolein, in particular acrolein. The reaction mixture consists of the catalyst dissolved in water and the 2-alkenal to be hydrated. The above-mentioned catalysts are contained in the reaction mixture in a total quantity of from 0.05 to 20 wt. %, preferably from 0.05 to 10 wt. % and in particular from 0.05 to 5 wt. %. Moreover the catalysts contained in aqueous solution can be buffered in the pH range of 2 to 5 by the addition of a base. Alkali metal hydroxides and alkaline-earth hydroxides as well as tertiary amines are suitable for this. The quantities of catalyst and 2-alkenal in the reaction mixture are coordinated with one another so that the reaction mixture forms a homogeneous phase during the reaction. A preferred initial concentration of 2-alkenal in the reaction mixture is in the range of from 6 to 20 wt. %, in particular from 10 to 18 wt. %. The hydration may take place within a wide temperature range; a temperature of from 20° to 80° C. is preferred. It is usual to operate under normal pressure. A slight excess pressure may usefully be applied at temperatures around or above the boiling point of the 2-alkenal used.

The catalysts used according to the invention are distinguished by their ready availability and the low cost of obtaining them. They have a very high activity with satisfactory selectivity. Especially worth mentioning are the high space-time yields achievable with these catalysts; compared with the known homogeneous catalysts, they are greater by one order of magnitude.

Chelate ion-exchange resins containing iminocarboxylic acid groups and phosphonic acid groups anchored to a polymer matrix are well-known as heterogeneous catalysts for the hydration of acrolein. However, the corresponding N-substituted monomeric analogs of the polymerically anchored groups surprisingly show almost no reactivity. Thus, for example, N-benzyliminodiacetic acid—the analog of the iminodiacetic acid bonded to a polystyrenedivinylbenzene resin—possesses virtually no activity in the hydration. The suitability as a homogeneous catalyst is therefore connected in particular with the existence of a hydrogen atom on the nitrogen atom (NH, "imino"), a fact hitherto unknown.

DETAILED DESCRIPTION OF THE PREFERRED EMBODIMENTS

EXAMPLES

Examples 1–7 and Comparative Examples CE 1–3

Acrolein is hydrated to 3-hydroxypropionaldehyde (HPA) in a double-jacketed reactor under the conditions given in Table 1. To this end, the acrolein is homogenized with the given quantity of water and, after the mixture has been thermostatted, the given quantity of catalyst is added thereto. The reaction mixture obtained having a defined initial acrolein concentration is stirred at the given reaction temperature for the given period of the reaction. Subsequently, the conversion of acrolein and the selectivity with respect to HPA are determined by HPLC and, from this, the space-time yield is determined. The conditions and results of Examples 1 to 7 and of Comparative Examples CE1 to CE3 are listed in Table 1.

Comparative Example CE1 shows that sodium hydrogen phosphate is a selective catalyst, but that it possesses only a very low activity. Buffer systems (CE2) also exhibit a comparatively low catalytic activity. N-Benzyliminodiacetic acid (CE3), which is the monomeric analog of a chelate ion-exchange resin based on polystyrene-divinylbenzene with iminodiacetic acid anchoring groups, possesses virtually no reactivity. By means of the iminophosphonic acid compounds and iminocarboxylic acid compounds according to the invention (Examples 1 to 7) it is possible to achieve activities distinctly greater in comparison, with at the same time satisfactory selectivity. Thus, in Examples 3 to 5 according to the invention, the space-time yields are greater than in the case of the Comparative Examples CE 1 to 3 by approximately a power of ten.

TABLE

| Ex. | Catalyst | Catalyst Quantity [g] [wt. %] | Water [g] | Acrolein [g] | Initial Acrolein Conc. [wt. %] | pH |
|---|---|---|---|---|---|---|
| VB1 | NaH$_2$PO$_4$ | 6.0/0.9 | 520 | 120 | 17.8 | 4.5 |
| VB2 | Acrylic acid buffered with triethylamine | 3.8/0.6 | 520 | 120 | 17.8 | 4.0 |
| VD3 | N-benzyliminodiacetic acid | 11.2/1.7 | 520 | 120 | 17.6 | 2.2 |
| 1 | Iminodiacetic acid | 6.6/1.0 | 520 | 120 | 17.9 | 2.0 |
| 2 | Iminodipropionic acid (monoammonium salt) | 8.9/1.4 | 520 | 120 | 17.8 | 4.8 |
| 3 | N-phosphonomethyl glycine | 8.5/1.3 | 520 | 120 | 17.8 | 1.7 |
| 4 | N-phosphonomethyl glycine (monoisopropyl ammonium salt) | 11.4/1.8 | 520 | 120 | 17.8 | 4.2 |
| 5 | Iminodimethylphosphonic salt | 10.3/1.6 | 520 | 120 | 17.8 | 1.2 |
| 6 | Iminodimethylphosphonic salt | 3.4/0.5 | 520 | 120 | 17.9 | 1.4 |
| 7 | Nitrilo-tris-methylenephosphonic acid | 15.0/2.3 | 520 | 120 | 17.7 | 1.2 |

| Ex. | Catalyst | Temp. [° C.] | Time [min] | Acrolein conversion [%] | Selectivity HPA [%] | RZA [g HPA/l*h] |
|---|---|---|---|---|---|---|
| VB1 | NaH$_2$PO$_4$ | 60 | 420 | 50 | 83 | 14 |
| VB2 | Acrylic acid buffered with triethylamine | 60 | 180 | 45 | 82 | 28 |
| VD3 | N-benzyliminodiacetic acid | 50 | 180 | 17 | 83 | 11 |
| 1 | Iminodiacetic acid | 50 | 30 | 30 | 66 | 91 |
|   |   |   | 60 | 52 | 66 | 79 |
| 2 | Iminodipropionic acid (monoammonium salt) | 50 | 30 | 25 | 55 | 63 |
|   |   |   | 60 | 30 | 50 | 34 |
| 3 | N-phosphonomethyl glycine | 50 | 30 | 70 | 67 | 216 |
|   |   |   | 60 | 93 | 62 | 113 |
| 4 | N-phosphonomethyl glycine (monoisopropyl ammonium salt) | 50 | 30 | 50 | 65 | 150 |
|   |   |   | 60 | 65 | 62 | 93 |
| 5 | Iminodimethylphosphonic salt | 50 | 10 | 45 | 63 | 393 |
|   |   |   | 20 | 65 | 60 | 270 |
| 6 | Iminodimethylphosphonic salt | 50 | 30 | 32 | 70 | 103 |
|   |   |   | 60 | 46 | 65 | 69 |
| 7 | Nitrilo-tris-methylenephosphonic acid | 50 | 30 | 20 | 66 | 61 |
|   |   |   | 60 | 31 | 62 | 44 |

What is claimed is:

1. A process for preparing 3-hydroxylalkanals having 3 to 12 carbon atoms, by hydration of a 2-alkenal with water in the presence of a catalyst in homogeneous phase at a reaction temperature of from 10 to 100° C., at a pressure of from 1 to 20 bar, at an initial concentration of the 2-alkenal in the reaction mixture of from 3 to 30 wt. %, wherein the catalyst used is a compound corresponding to the formula:

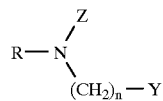

wherein

Z denotes H, $C_1$- to $C_6$-alkyl, —$CH_2$—$CH(CH_3)$—Y' or —$(CH_2)_o$—Y';

R denotes H;

Y and Y' are identical or different and denote —COOH, —$P(O)(OH)_2$, —OH, pyridyl, or —$P(O)(CH_2OH)OH$, wherein the acid functional group may be present partly in the form of its alkali metal salt, alkaline-earth salt or ammonium salt;

n denotes 1, 2, 3, 4, 5 or 6 where Y is —COOH, —$P(O)(OH)_2$, pyridyl or —$P(O)(CH_2OH)OH$; 2 or 3 where Y is —OH, o denotes 1, 2, 3, 4, 5 or 6 where Y' is —COOH, —$P(O)(OH)_2$, pyridyl or —$P(O)(CH_2OH)OH$; 0, 2 or 3 where Y' is —OH.

2. A process as claimed in claim 1, wherein the catalyst comprises a compound selected from the group consisting of iminodiacetic acid, iminodipropionic acid, iminodimethylphosphonic acid, N-phosphonomethylglycine and salts thereof.

3. A process as claimed in claim 1, wherein the 3-hydroxyalkanals have 3 or 4 carbon atoms.

4. A process as claimed in claim 3, wherein the catalyst comprises a compound selected from the group consisting of iminodiacetic acid, iminodipropionic acid, iminodimethylphosphonic acid, N-phosphonomethylglycine and salts thereof.

* * * * *